Feb. 23, 1932. G. B. HART Plant Pat. 8
ROSE
Filed May 12, 1931
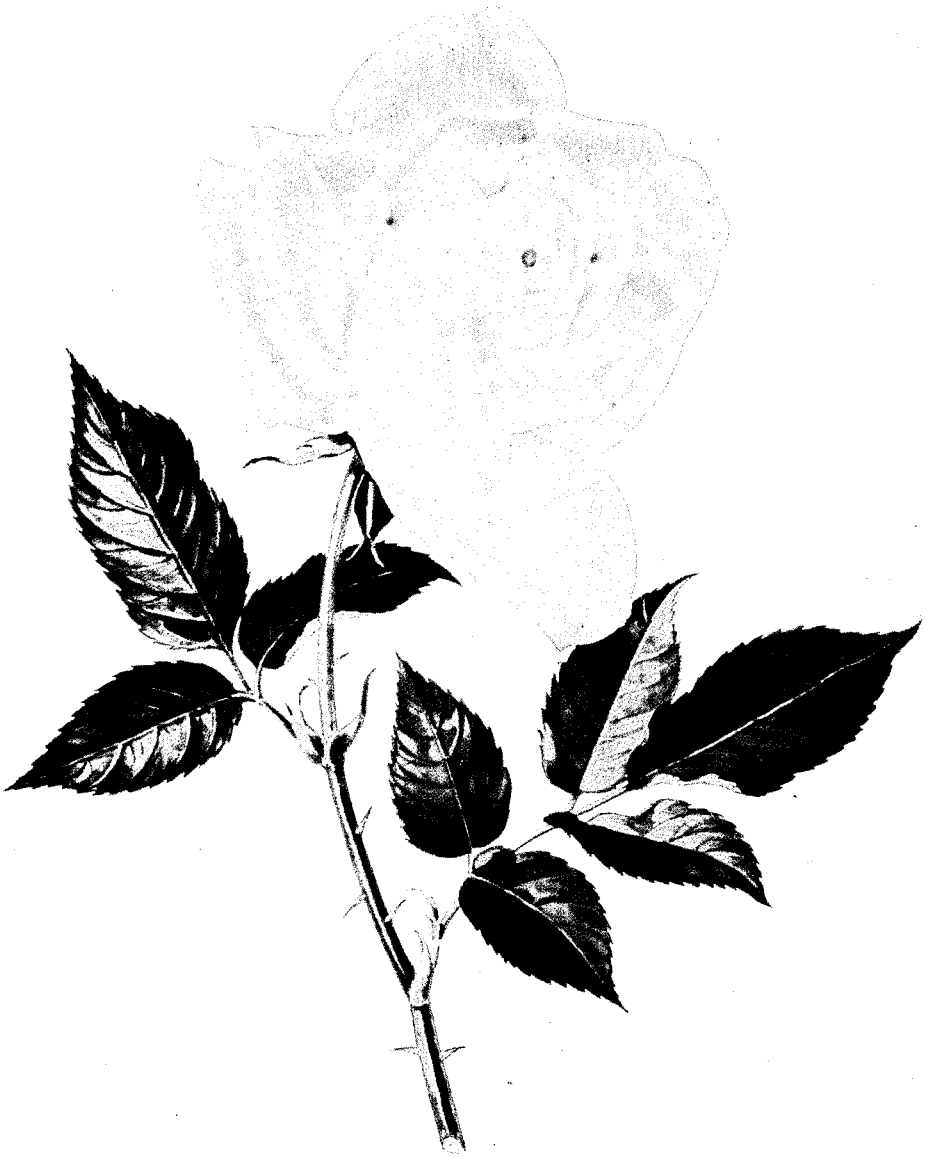
Inventor
George B. Hart
By Frank Keifer
Attorney Patented Feb. 23, 1932

Plant Pat. 8

UNITED STATES PATENT OFFICE

GEORGE B. HART, OF BRIGHTON, NEW YORK

ROSE

Application filed May 12, 1931. Serial No. 536,804.

The object of this invention or discovery is to provide a distinct and new variety of rose and a distinct and new variety of plant bearing said rose, said rose having petals of a red color of a shade between the colors of spectrum red and carmine, so-called, which colors are shown on Ridgeway's color chart, to the colors in which chart reference is made.

These and other features of the invention or discovery will be illustrated in the drawing, described in the specification and pointed out in the claim at the end thereof.

In the drawing is shown a perspective view of the rose, its petals, stem and leaves being shown in natural colors.

This invention or discovery pertains to hybrid tea roses and plants for bearing such roses and has for its object the production of a distinct and new variety of red hybrid tea rose, the color of the petals of which is between the colors of spectrum red and carmine, so-called, as shown on Ridgeway's color chart. This rose and the plant bearing it originated as a sport on the Talisman hybrid tea rose, so-called, and has been asexually reproduced as a distinct and new variety of plant, being a hybrid tea rose bush or plant which bears and is capable of bearing red hybrid tea roses having petals of the shade or color above described.

One of the leading characteristics of this rose aside from the color of the petals above mentioned, is the absence of blue at any time in the petals either while the rose is in full bloom or while the rose is fading.

This rose and the plant bearing it originated as a sport on the Talisman hybrid tea rose, so-called, and has been asexually reproduced by both budding and grafting and the plants or rose bushes so reproduced have borne roses having all of the above characteristics, said roses also having the characteristics, except as to color, of the Talisman hybrid tea rose produced by the Talisman hybrid tea rose plant or bush on which the sport originated which first produced this distinct and new variety of rose and from which sport the distinct and new variety of plants or bushes bearing this distinct and new variety of rose has been asexually propagated or reproduced.

It will also be understood that the distinct and new variety of plant bearing this distinct and new variety of rose is to all outward appearances substantially the same as the plant that regularly bears the so-called Talisman rose.

I claim:

The new variety of rose bush, herein shown and described, characterized by having roses in which the petals are a red color of a shade between spectrum red and carmine.

In testimony whereof I affix my signature.

GEORGE B. HART.